(12) United States Patent
Watanabe et al.

(10) Patent No.: US 9,745,237 B2
(45) Date of Patent: Aug. 29, 2017

(54) GENERATION METHOD FOR GENERATING 3, 5-DIHYDROXY-4-METHOXYBENZYL ALCOHOL FROM OYSTER MEAT

(71) Applicant: Watanabe Oyster Laboratory Co., Ltd., Tokyo (JP)

(72) Inventors: Mitsugu Watanabe, Tokyo (JP); Takayuki Watanabe, Tokyo (JP); Hideaki Watanabe, Tokyo (JP)

(73) Assignee: WATANABE OYSTER LABORATORY CO., LTD., Tokyo (JP)

( * ) Notice: Subject to any disclaimer, the term of this patent is extended or adjusted under 35 U.S.C. 154(b) by 0 days.

(21) Appl. No.: 14/896,433

(22) PCT Filed: Sep. 2, 2014

(86) PCT No.: PCT/JP2014/004504
§ 371 (c)(1),
(2) Date: Dec. 7, 2015

(87) PCT Pub. No.: WO2016/027295
PCT Pub. Date: Feb. 25, 2016

(65) Prior Publication Data
US 2016/0200653 A1   Jul. 14, 2016

(30) Foreign Application Priority Data
Aug. 22, 2014   (JP) ................. 2014-169316

(51) Int. Cl.
C07C 37/00   (2006.01)
C07C 41/44   (2006.01)
A23L 17/00   (2016.01)
C09K 15/08   (2006.01)

(52) U.S. Cl.
CPC ............ *C07C 37/004* (2013.01); *A23L 17/00* (2016.08); *C07C 41/44* (2013.01); *C09K 15/08* (2013.01)

(58) Field of Classification Search
None
See application file for complete search history.

(56) References Cited

U.S. PATENT DOCUMENTS

2013/0303629 A1   11/2013   Watanabe et al.

FOREIGN PATENT DOCUMENTS

| EP | 2 669 353 | 12/2013 |
|---|---|---|
| JP | 09-135673 | * 5/1997 |
| JP | 10-136946 | 5/1998 |
| JP | 10-338640 | 12/1998 |
| JP | 2001-149049 | * 6/2001 |
| JP | 2009-060869 | 3/2009 |
| JP | 2010-193756 | 9/2010 |
| JP | 2012-153852 | 8/2012 |
| WO | 2012/102044 | 8/2012 |

OTHER PUBLICATIONS

International Search Report dated Oct. 28, 2014 in International Application No. PCT/JP2014/004504.
Written Opinion of the International Searching Authority dated Oct. 28, 2014 in International Application No. PCT/JP2014/004504.
Watanabe M., et al., Isolation and Characterization of a Phenolic Antioxidant from the Pacific Oyster (*Crassostrea gigas*), J. Agric. Food Chem., 2012, vol. 60, No. 3, p. 830-835.
Watanabe M., et al., "A phenolic antioxidant from the Pacific oyster (*Crassostrea gigas*) inhibits oxidation of cultured human hepatocytes mediated by diphenyl-1-pyrenylphosphine", Food Chem., 2012, vol. 134, No. 4, p. 2086-2089.
Kasumi Ohashi et al., "Kaki Yurai Shinki Kosanka Busshitsu 3,5-dihydroxy-4-methoxybenzyl alcohol no Kaiba Glutamic Acid Sadosei Shinkei Katsudo ni Taisuru Sayo Kaiseki", Abstracts of Annual Meeting of Pharmaceutical Society of Japan (CD-ROM), Mar. 5, 2014, vol. 134, p. 195 (30V-am03S).
Hiroaki Okabe et al., "LC-MS/MS ni yoru Magaki Yurai Phenol-sei Kosanka Busshitsu no Teiryo", Rinsho Kagaku, Aug. 31, 2014, vol. 43, supplementary issue 1, p. 259 (81).

* cited by examiner

*Primary Examiner* — Rosalynd Keys
(74) *Attorney, Agent, or Firm* — Wenderoth, Lind & Ponack, L.L.P.

(57) ABSTRACT

Problem

The present invention is to provide a generation method that can generate 3,5-dihydroxy-4-methoxybenzyl alcohol, which was not found at all from raw oyster meat originally, at an extraction phase of oyster meat essence.

Solution

The present invention heats raw oyster meat from which 3,5-dihydroxy-4-methoxybenzyl alcohol is not detected in a raw state at 98° C. to 100° C. for six hours or more to generate 3,5-dihydroxy-4-methoxybenyl alcohol from oyster meat liquid on which the heating process has been performed.

4 Claims, 18 Drawing Sheets

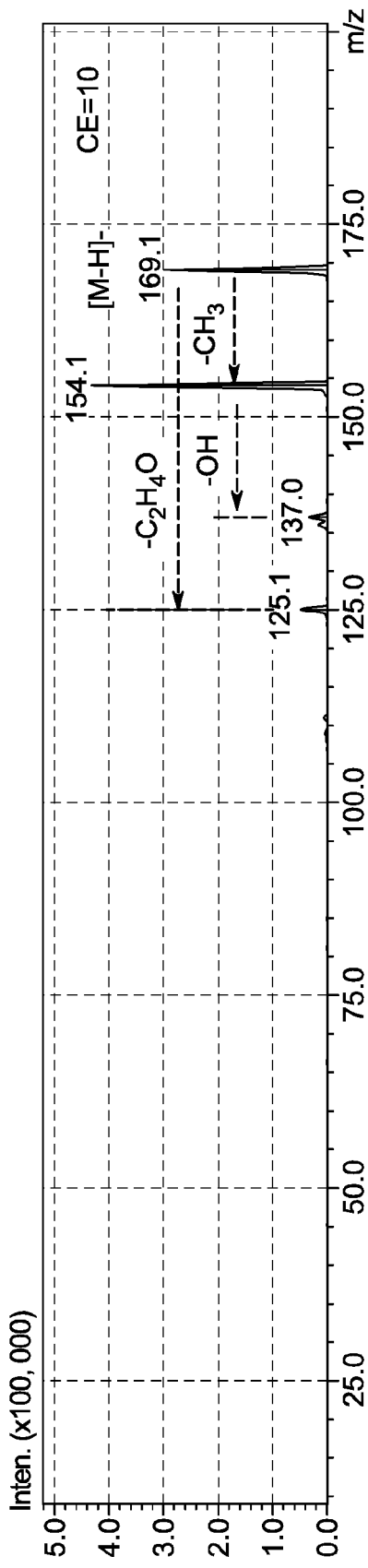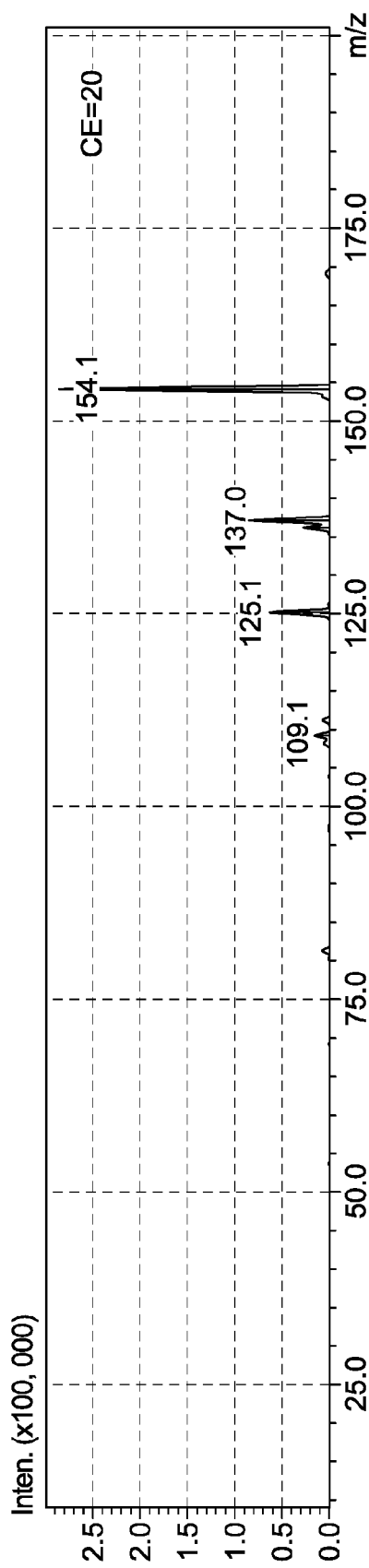
PRODUCTION OF E6 STANDARD SPECIMEN OF 10,000 ng/ml (precursor ion : m/z 169.10)
FIG. 4

MRM CHROMATOGRAM OF E6 STANDARD SPECIMEN OF 100 ng/ml

CALIBRATION CURVE OF E6 STANDARD SPECIMEN

MRM CHROMATOGRAM OF E6 IN SAMPLE HEATED AT STANDARD PRESSURE FOR TWO HOURS AFTER OYSTER ESSENCE EXTRACTION

MRM CHROMATOGRAM OF E6 IN SAMPLE HEATED AT 3 atm FOR TWO HOURS AFTER OYSTER ESSENCE EXTRACTION

Fig.11

LC-MS/MS ANALYSIS RESULTS OF E6 IN HEATING EXPERIMENT SAMPLE AT STANDARD PRESSURE (TEMPORAL COMPARISON)

| | RAW OYSTER | OYSTER ESSENCE (1 atm, 1h) | HEATED AT 1 atm FOR TWO HOURS AFTER OYSTER ESSENCE EXTRACTION |
|---|---|---|---|
| TEMPERATURE | | 92~94°C | 92~94°C |
| LIQUID MEASURE | 1 kg | 681.34 g | 602.07 g |
| VOLUME PROPORTION | | 100% | 88% |
| E6 CONCENTRATION μg/mL | N.D. | N.D. | N.D. |
| TOTAL AMOUNT OF E6 (IN UNITS OF OYSTER 1 kg) | N.D. | | |

| | HEATED AT 1 atm FOR FOUR HOURS AFTER OYSTER ESSENCE EXTRACTION | HEATED AT 1 atm FOR SIX HOURS AFTER OYSTER ESSENCE EXTRACTION | HEATED AT 1 atm FOR EIGHT HOURS AFTER OYSTER ESSENCE EXTRACTION |
|---|---|---|---|
| TEMPERATURE | 92~94°C | 92~94°C | 92~94°C |
| LIQUID MEASURE | 568.42 g | 529.38 g | 481.73 g |
| VOLUME PROPORTION | 83% | 78% | 71% |
| E6 CONCENTRATION μg/mL | .09 ± 0.04 (QUANTITATIVE LIMIT OR LESS) | 0.12 ± 0.09 (QUANTITATIVE LIMIT OR LESS) | 0.29 ± 0.08 (QUANTITATIVE LIMIT OR LESS) |
| TOTAL AMOUNT OF E6 (IN UNITS OF OYSTER 1 kg) | 51.2 ± 22.7 (QUANTITATIVE LIMIT OR LESS) | 63.5 ± 47.6 (QUANTITATIVE LIMIT OR LESS) | 139.7 ± 38.5 (QUANTITATIVE LIMIT OR LESS) |

QUANTITATIVE LIMIT 0.5μg/mL

Fig.12

LC-MS/MS ANALYSIS RESULTS OF E6 IN HEATING EXPERIMENT SAMPLE (TEMPORAL COMPARISON)

| | HEATED AT 1 atm FOR 8 HOURS AFTER OYSTER ESSENCE EXTRACTION | HEATED AT 1 atm FOR 12 HOURS AFTER OYSTER ESSENCE EXTRACTION | HEATED AT 1 atm FOR 13 HOURS AFTER OYSTER ESSENCE EXTRACTION |
|---|---|---|---|
| TEMPERATURE | 92-94°C | 92-94°C | 92-94°C |
| LIQUID MEASURE | 399.63 g | 336.33 g | 263.33 g |
| VOLUME PROPORTION | 59% | 49% | 39% |
| E6 CONCENTRATION (μg/mL) | 0.54 ± 0.04 | 0.86 ± 0.18 | 1.42 ± 0.26 |
| TOTAL AMOUNT OF E6 (IN UNITS OF OYSTER 1 kg) | 215.8 ± 18.0 | 288.4 ± 60.4 | 373.9 ± 68.5 |

| | HEATED AT 1 atm FOR 16 HOURS AFTER OYSTER ESSENCE EXTRACTION | HEATED AT 1 atm FOR 17 HOURS AFTER OYSTER ESSENCE EXTRACTION | HEATED AT 1 atm FOR 19 HOURS AFTER OYSTER ESSENCE EXTRACTION | HEATED AT 1 atm FOR 20 HOURS AFTER OYSTER ESSENCE EXTRACTION |
|---|---|---|---|---|
| TEMPERATURE | 92-94°C | 92-94°C | 92-94°C | 92-94°C |
| LIQUID MEASURE | 181.98 g | 151.89 g | 125.38 g | 89.57 g |
| VOLUME PROPORTION | 27% | 22% | 18% | 13% |
| E6 CONCENTRATION (μg/mL) | 2.83 ± 0.03 | 3.42 ± 0.30 | 4.88 ± 0.10 | 6.49 ± 0.19 |
| TOTAL AMOUNT OF E6 (IN UNITS OF OYSTER 1 kg) | 478.6 ± 5.5 | 519.5 ± 45.6 | 609.3 ± 12.3 | 581.3 ± 17.0 |

QUANTITATIVE LIMIT 0.5 μg/mL

Fig.13

LC-MS/MS ANALYSIS RESULTS OF E6 IN PRESSURIZATION/HEATING EXPERIMENT SAMPLE USING PRESSURE COOKER

| | RAW OYSTER | OYSTER ESSENCE (1 atm, 2h) | AT 2 atm FOR ONE HOUR AFTER OYSTER ESSENCE EXTRACTION | AT 3 atm FOR TWO HOURS AFTER OYSTER ESSENCE EXTRACTION |
|---|---|---|---|---|
| TEMPERATURE | | 92°C | 135°C | 135°C |
| LIQUID MEASURE | 20 kg | 23 kg | 21.2 kg | 19.1 kg |
| | | 100% | 92% | 83% |
| E6 CONCENTRATION ($\mu$g/mL) | N.D. | N.D. | 1.7 ± 0.10 | 3.5 ± 0.39 |
| TOTAL AMOUNT OF E6 $\mu$g (IN UNITS OF OYSTER 1 kg) | N.D. | N.D. | 1802 ± 106.0 | 3342.5 ± 372.5 |
| QUANTITATIVE LIMIT 0.5 $\mu$g/mL | | | | |

USED DEVICE : OAMVP α-C-08EL (KAJIWARA INC.)

NOTE THAT SPECIFIC GRAVITY OF SAMPLE TO WHICH ETHANOL IS ADDED SO AS TO BE 70% AFTER EXTRACTING SAMPLE WAS ASSUMED AS 1, SO NEEDS TO BE RECALCULATED.

ANALYSIS RESULT

TO WATANABE OYSTER LABORATORY

REQUEST SUMMARY
   SPECIMEN ①3,5-dihydroxy-4-methoxybenzyl alcohol
                ② CONCENTRATED-OYSTER MEAT EXTRACTED ESSENCE
   USED DEVICE   SHIMAZU HIGH-PERFORMANCE LIQUID CHROMATOGRAPH LC-2010 SYSTEM PURPOSE OF ANALYSIS   ANALYSIS OF 3, 5-dihydroxy-4-methoxybenzyl alcohol IN CONCENTRATED-OYSTER MEAT EXTRACTED ESSENCE

METHOD AND RESULTS OF ANALYSIS

- The Shim-pack CLC-ODS (250 mmL × 4.6 mm i.d., 5 µm) WAS USED AS A COLUMN TO SEPARATE THE SPECIMEN. ABSORBANCE WAS DETECTED AT A WAVELENGTH OF 210 nm. FOR DETAILS OF ANALYSIS CONDITIONS, REFER TO <SEPARATE SHEET-1>.

- The kept 3, 5-dihydroxy-4-methoxybenzyl alcohol was dissolved to prepare 30 µg/ml (35% methanol) solution and the solution was injected to the HPLC. The results are shown in Fig.1.

- 5% OF FORMIC ACID WAS ADDED TO THE KEPT CONCENTRATED-OYSTER MEAT EXTRACTED ESSENCE TO MAKE A SPECIMEN SOLUTION AND THE SOLUTION WAS INJECTED TO THE HPLC. THE RESULTS ARE SHOWN IN Fig.2.
3,5-dihydroxy-4-methoxybenzyl alcohol IN THE CONCENTRATED -OYSTER MEAT EXTRACTED ESSENCE WAS CALCULATED AS APPROXIMATELY 30 µg/ml.

PERSON IN CHARGE OF ANALYSIS   KEIKO YAMABE   STAMP OF APPROVAL

DOCUMENT NO.42331

SHIMADZU
Solutions for science
since 1875

FIG. 14

<SEPARATE SHEET-1>
ANALYSIS CONDITION

COLUMN : Shim-pack CLC-ODS(M) (250 mmL×4.6 mmi.d., 5 μm)
MOBILE PHASE : A; WATER
B; ACETONITRILE
B.Conc 7.5%(0-10 min) → 100%(10.01-15 min)
→ 7.5%(15.01-22 min)
FLOW RATE : 1.0 mL / min
MIXER : 0.27 mL
COLUMN TEMPERATURE : 25 °C
AMOUNT OF INJECTION : 10 μL
DETECTION : ABSORBANCE DETECTION
MEASURED WAVELENGTH : 210nm
LAMP : D2
CELL : STANDARD DETAILS OF ANNEX
Fig.1 : RESULTS OF STANDARD SOLUTION (30 μg/ml)
Fig.2 : RESULTS OF SPECIMEN

DOCUMENT NO.42331

SHIMADZU
Solutions for science
since 1875

FIG. 15

Fig.1 RESULTS OF STANDARD SOLUTION (30 μg/ml)

Fig. 2 RESULTS OF SPECIMEN SOLUTION

GENERATION METHOD FOR GENERATING 3, 5-DIHYDROXY-4-METHOXYBENZYL ALCOHOL FROM OYSTER MEAT

TECHNICAL FIELD

The present invention relates to a generation method for generating 3,5-dihydroxy-4-methoxybenzyl alcohol from an oyster meat.

BACKGROUND ART

An oyster, for example, Crassostreagigas is a bivalve belonging to a family Ostreidae in the order Pterioida. The habitat covers the entire East Asia region including Japan. Nowadays, the Crassostreagigas is also cultivated in France and Australia, and is renowned as the most eaten oyster in the world.

Since it is highly nutritious, the oyster has been used for food since ancient times. As described above, the oyster contains a large amount of minerals such as calcium, zinc, selenium, copper, manganese, or a similar material as well as glycogen and protein.

As an antioxidant material derived from the oyster, SOD, CAT, GPx, and Prx6 are reported as an enzymatic antioxidant substance, and metallothionein, uncouplingprotein5 (UCP5), ascorbic acid, α-tocopherol, and β-carotene are reported as a non-enzymatic antioxidant substance.

[Patent document 1] Japanese Unexamined Patent Application Publication No. 2010-193756

DISCLOSURE OF THE INVENTION

Problems to be Solved by the Invention

Recently, the inventor of the present invention has succeeded to find a so-called novel and excellent antioxidant substance from an oyster, 3,5-dihydroxy-4-methoxybenzyl alcohol. The inventor has also succeeded to determine the chemical constitution and conduct the chemosynthesis of the antioxidant substance. Thus, the inventor has succeeded to provide a so-called novel and excellent antioxidant and antioxidant composition whose active ingredient is 3,5-dihydroxy-4-methoxybenzyl alcohol in both cases where the substance is not derived from the oyster and is derived from the oyster.

However, from the inside of the raw oyster meat, 3,5-dihydroxy-4-methoxybenzyl alcohol has not found. It has not been confirmed what extraction and production extract and generate the active ingredient called the 3,5-dihydroxy-4-methoxybenzyl alcohol from the raw oyster meat.

Thus, when generating oyster meat essence containing many active ingredients from the raw oyster meat, the inventor of the present invention has succeeded to find a generation method. The generation method can generate 3,5-dihydroxy-4-methoxybenzyl alcohol, which was not found at all from the raw oyster meat originally, at an extraction phase of the oyster meat essence.

Thus, the object of the present invention is to provide the generation method that can generate 3,5-dihydroxy-4-methoxybenzyl alcohol, which was not found at all from the raw oyster meat originally, at the extraction phase of the oyster meat essence.

Means for Solving the Problem

The present invention heats raw oyster meat from which 3,5-dihydroxy-4-methoxybenzyl alcohol is not detected in a raw state at 98° C. to 100° C. for six hours or more to generate 3,5-dihydroxy-4-methoxybenzyl alcohol from oyster meat liquid on which the heating process has been performed. Alternatively, the present invention heats raw oyster meat from which 3,5-dihydroxy-4-methoxybenzyl alcohol is not detected in a raw state at 90° C. or more for at least nine hours or more to generate 3,5-dihydroxy-4-methoxybenzyl alcohol from oyster meat liquid on which the heating process has been performed. Alternatively, the present invention puts raw oyster meat from which 3,5-dihydroxy-4-methoxybenzyl alcohol is not detected in a raw state in an extraction container to extract oyster meat essence, heats extracted oyster meat essence extract liquid at a state of one atmospheric pressure at 90° C. or more for at least ten hours or more to generate 3,5-dihydroxy-4-methoxybenzyl alcohol from the heated oyster meat extract liquid. Alternatively, the present invention heats raw oyster meat from which 3,5-dihydroxy-4-methoxybenzyl alcohol is not detected in a raw state in a pressurized state of one atmospheric pressure or more to generate 3,5-dihydroxy-4-methoxybenzyl alcohol from oyster meat liquid heated in the pressurized state. Alternatively, the present invention heats raw oyster meat from which 3,5-dihydroxy-4-methoxybenzyl alcohol is not detected in a raw state in a pressurized state of three atmospheric pressures or more at 90° C. or more for at least one hour or more to generate 3,5-dihydroxy-4-methoxybenzyl alcohol from oyster meat liquid heated in the pressurized state. Alternatively, the present invention puts raw oyster meat from which 3,5-dihydroxy-4-methoxybenzyl alcohol is not detected in a raw state in an extraction container to extract oyster meat essence, heats extracted oyster meat essence extract liquid in a pressurized state of three atmospheric pressures or more at 90° C. or more for at least one hours or more to generate 3,5-dihydroxy-4-methoxybenzyl alcohol from the oyster meat essence extract liquid heated in the pressurized state.

Advantages of the Invention

According to the present invention, the following excellent effect is achieved. 3,5-dihydroxy-4-methoxybenzyl alcohol, which was not found at all from the raw oyster meat originally, can be generated by heating or pressurizing the oyster meat.

BRIEF DESCRIPTION OF DRAWINGS

FIG. 11, is an explanatory view showing LC-MS/MS analysis results of E6 in a heating experiment sample at a standard pressure;

FIG. 12 is an explanatory view showing LC-MS/MS analysis results of E6 in a healing experiment sample at a standard pressure;

FIG. 13 is an explanatory view showing LC-MS/MS analysis results of E6 in a pressurization/heating experiment sample using a pressure cooker;

FIG. 14 is an explanatory view showing an analysis result;

FIG. 15 is an explanatory view describing analysis conditions;

BEST MODE FOR CARRYING OUT THE INVENTION

Figure 1:
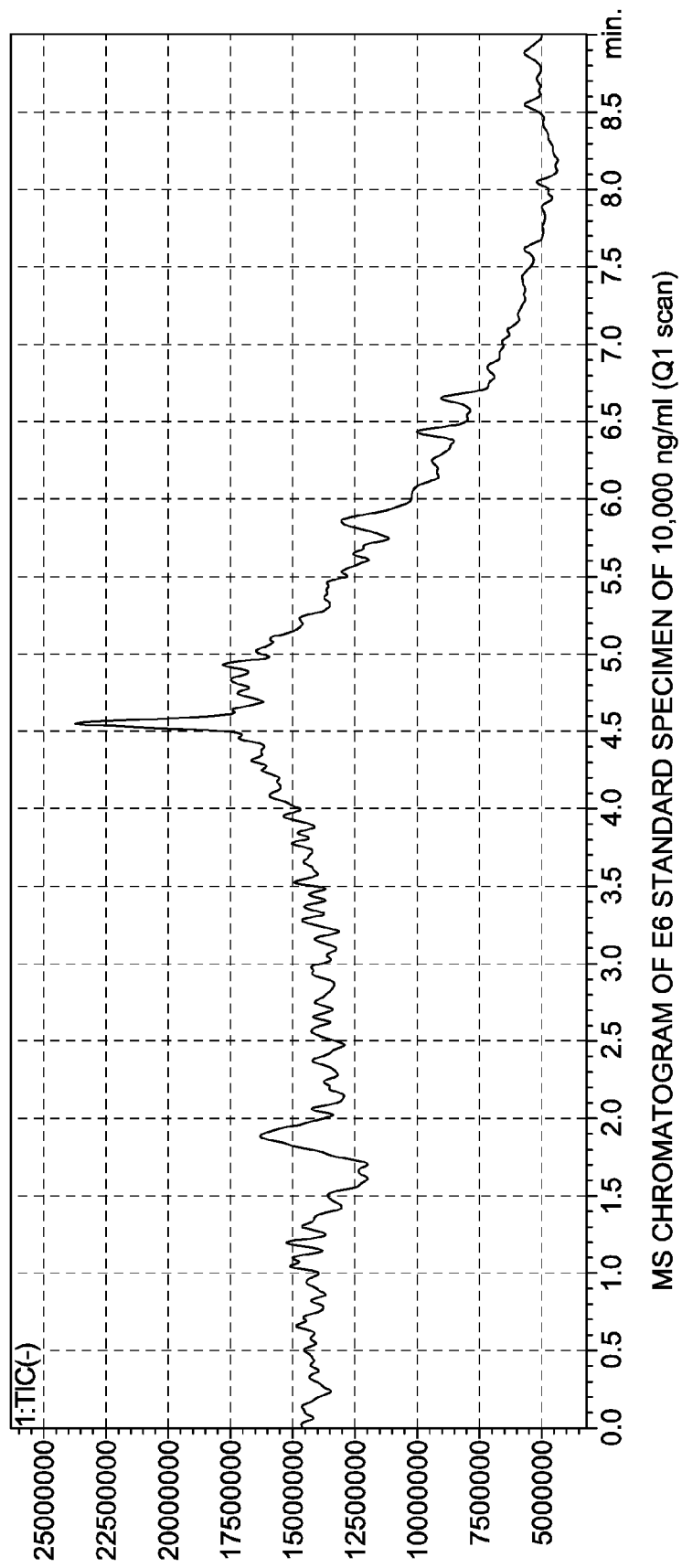
FIG. 1 is an explanatory view illustrating an MS chromatogram (Q1 scan) of an E6 standard specimen of 10,000 ng/mL.

The following describes the present invention based on one working example illustrated in the drawings.

Working Example (Measurement Device and Measurement Method)

A high-performance chromatograph mass spectrometer (LCMS-8040: manufactured by SHIMADZU) was used for determination on whether 3,5-dihydroxy-4-methoxybenzyl alcohol (hereinafter referred to as E6) was present in raw oyster meat and an extract liquid of oyster meat essence or not and for measurement and analysis of at which concentration E6 was present.

1) Analysis Conditions of LC-MS/MS

Table 1 lists the analysis conditions for LC-MS/MS. LC analysis condition: as a separation column, Shim-Pack VP-ODS (150 mmL×2.0 mm I.D., 5 μm), which is an ODS column, was used. Using 0.05% acetic acid aqueous solution for a mobile phase A and acetonitrile for a mobile phase B, a gradient analysis (mobile phase B: 0 min: 5%→7 min: 100%→9.5 min: 5%→14 min: 5%) was conducted. A flow rate of 0.25 mL/min and a column oven temperature of 40° C. were set. An amount of injection of specimen was set to 1 μL. Since E6 is detected in a negative ion mode, the measurements were all performed in the negative ion mode. MS/MS analysis condition: as an ionization method, Electrospray Ionization (ESI method) was used. As parameters of MS, a DL temperature: 250° C., a nebulizer gas: flow rate 3 L/min, a heat block (BH) temperature: 400° C., and a dry-in gas flow rate: 15 L/min were set.

Table 1. Setting Values of Respective Parameters of LC-MS/MS

TABLE 1

Setting Values of Respective Parameters of LC-MS/MS

| | Parameter | Setting value |
|---|---|---|
| LC | Model | Prominence (Shimazu Corporation) |
| | Column | Shim-Pack VP-ODS (150 mmL × 2.0 mm i.d., 5 μm) |

TABLE 1-continued

Setting Values of Respective Parameters of LC-MS/MS

| | Parameter | Setting value |
|---|---|---|
| | Column temperature | 40° C. |
| | Mobile phase A | 0.05% acetic acid aqueous solution |
| | Mobile phase B | Acetonitrile |
| | Gradient condition | B: 5% (0 min)→100% (5 min)→5% (7.5 min)→5% (12 min) |
| MS/MS | Flow rate | 0.25 mL/min |
| | Amount of injection | 1 μM |
| | Model | LOMS-8040 (Shimazu Corporation) |
| | Ionization method | Electrosprey Ionization (ESI) Negative |
| | Nebulizer gas flow rate | 3 L/min |
| | Dry-in gas flow rate | 15 L/min |
| | Dl temperature | 250° C. |
| | Heat block temperature | 400° C. |

2) MS Spectrum of E6 Standard Specimen

First, a specimen of E6 becoming a criterion was generated. Using this standard specimen of E6, various analyses were conducted. From the respective analysis results, what property was owned by E6 was confirmed.

Figure 2:
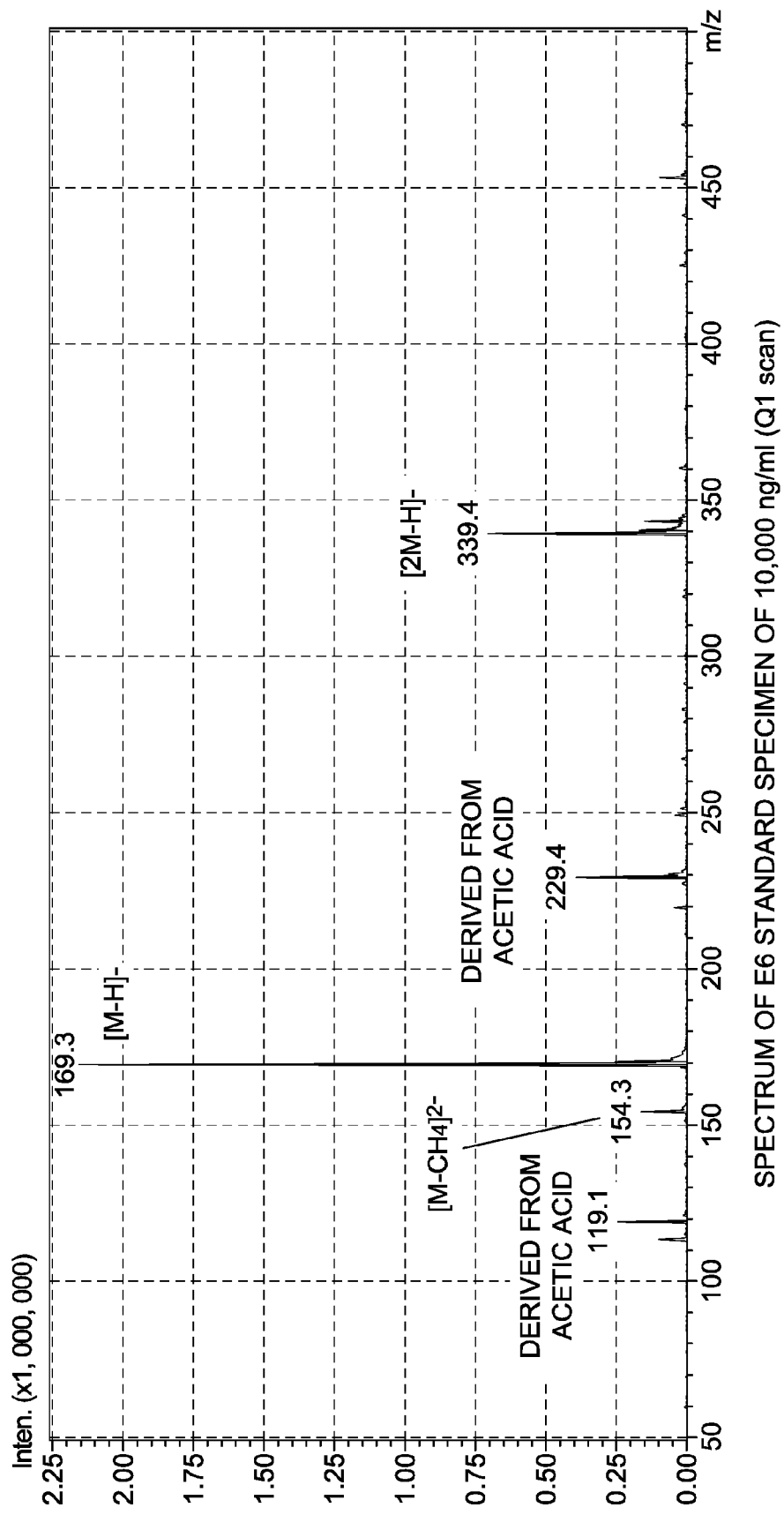
FIG. 2 is an explanatory view illustrating an MS spectrum (Q1 scan) of the E6 standard specimen of 10,000 ng/mL.

First, the standard specimen of E6 of 10,000 ng/mL was measured with a Q1 scan (MS range m/z: 50 to 500). The peak was detected at a holding time from 4.4 to 4.6 minutes (FIG. 1). From the MS spectrum at this peak part, as a signal derived from E6, precursor ion, which is a deprotonated ion $[M-H]^-$, at m/z of 169.3 was able to be confirmed (FIG. 2).

3) Product Ion Scan Spectrum of Standard Specimen of E6

Next, for qualitative analysis, the Q1 scan and a product ion scan were employed. In the product ion scan, a precursor ion, which is the deprotonated ion $[M-H]^-$ of the E6, at m/z of 169.1 was set and the analysis was conducted at collision energies 10 V, 20 V, and 30 V.

Figure 3:
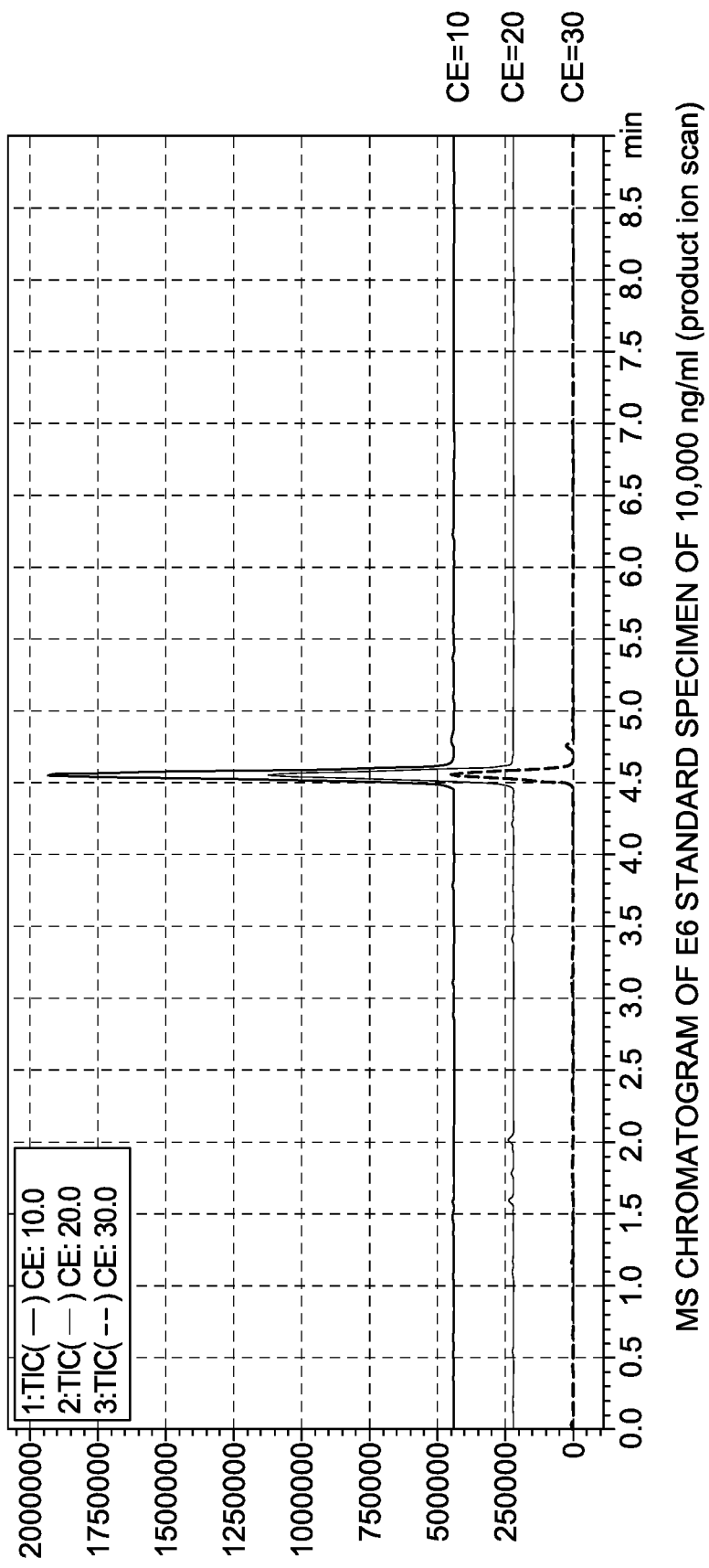
FIG. 3 is an explanatory view illustrating an MS chromatogram (product ion scan) of an E6 standard specimen of 10,000 ng/mL.
Figure 4:
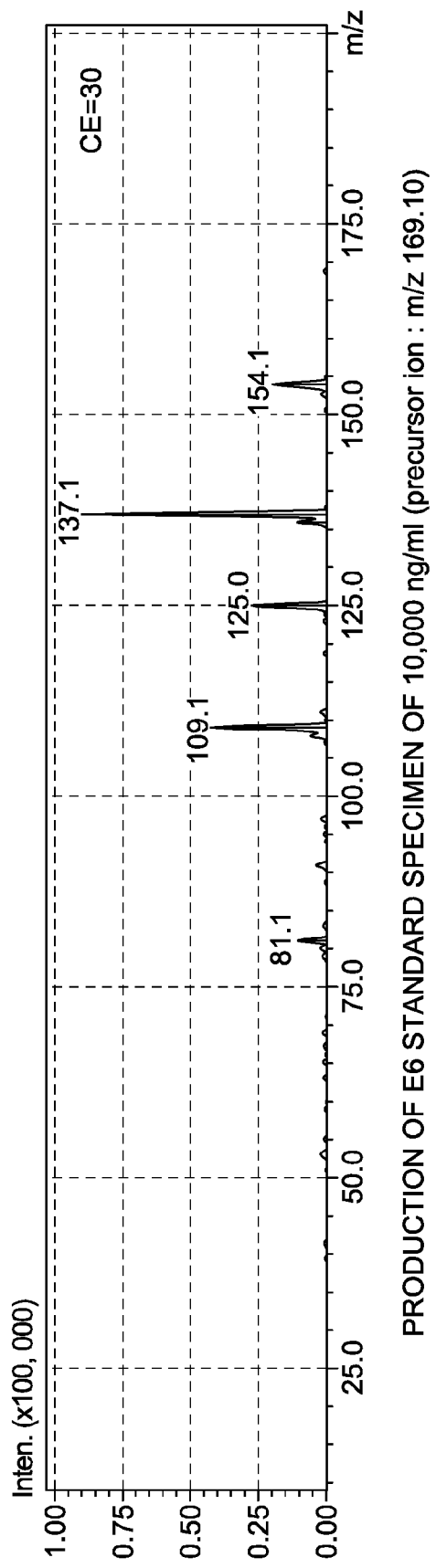
FIG. 4 is an explanatory view-illustrating a product ion (precursor ion: m/z at 169.10) of an E6 standard specimen of 10.000 ng/mL.

In the product ion scan on the standard specimen of E6 of 10,000 ng/mL, the peak was detected at the holding time from 4.4 to 4.6 minutes (FIG. 3). From the MS spectrum derived from the peak part (FIG. 4), a pattern of the product ion of the standard specimen of E6 was able to be obtained.

4) MRM Chromatogram of Standard Specimen of E6

Multiple reaction monitoring (MRM) was employed for the quantitative analysis. The MRM transition was decided by automatic optimization. Q1/Q3=169.1/154.1 (quantitative transition) and 169.1/136.9 and 169.1/125.1 (qualitative transition) were employed. Collision energies were each set to 15 V, 28 V, and 13 V.

Figure 5:
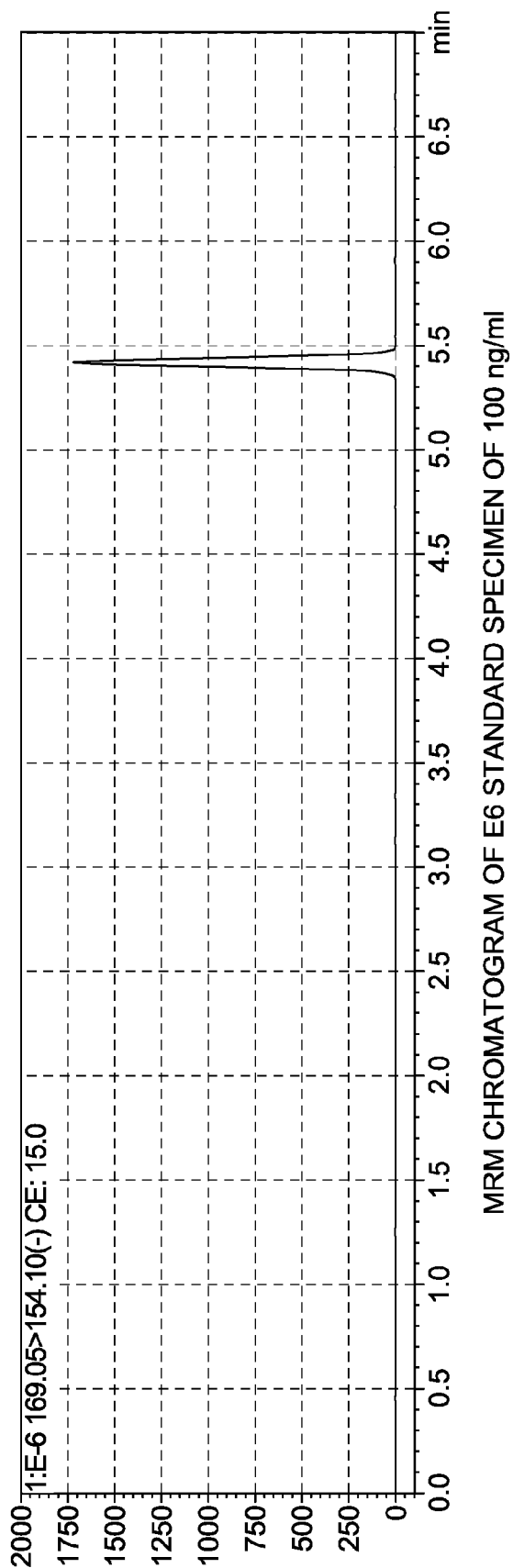
FIG. 5 is an explanatory view illustrating an MRM chromatogram of an E6 standard specimen of 100 ng/mL.

Under the above-described conditions, an MRM chromatogram of the standard specimen of E6 of 100 ng/mL was measured. The peak was detected at the holding time from 5.2 to 5.5 minutes (FIG. 5). The transition unique to E6 (Q1/Q3=169.1/154.1, 169.1/136.9, and 169.1/125.1) was detected. This confirmed that the peak was E6.

Due to, for example, an installation environment of a device for pump pressure of LC or a similar device, the holding time may slightly differ. However, Q1/Q3=169.1/154.1, 169.1/136.9, and 169.1/125.1 never vary.

5) Quantitative Analysis of E6

The standard specimen of E6 (1 to 1,000 ng/mL) was measured three times at each concentration by the MRM and a calibration curve of E6 was created. A correlation coefficient R of the calibration curve was 0.99991. Regarding the use of this calibration curve, heating and pressurization processes were performed on an extract liquid of oyster meat essence, the property of the sample was compared with this calibration curve, and values at the respective E6 concentrations were detected. Thus, the calibration curve is used.

The detection results of analysis on E6, that is, the specimen becoming a criterion for 3,5-dihydroxy-4-methoxybenzyl alcohol, are described above.

When heating and pressurizing an extract liquid from an oyster meat, which will be described later, for a predetermined time, the identical detection result is obtained and the identical property is obtained. Additionally, the extract liquid is heated and pressurized for the predetermined time. Then, it will be proved that E6, that is, 3,5-dihydroxy-4-methoxybenzyl alcohol, is observed.

6) MRM Chromatogram of Heating/Pressurization Experiment Sample

First, the raw oyster meat was pressurized, squashed, and liquefied. Then, in the liquefied raw oyster, at which concentration of E6, that is, 3,5-dihydroxy-4-methoxybenzyl alcohol was present or not was measured.

However, in the liquefied raw oyster, the peak was not observed at the holding time from 5.2 to 5.5 minutes at all. In the sample generated by pressurizing, squashing, and liquefying this raw oyster meat, E6 was not able to be observed at all.

Next, heating experiment (no pressure) added pure water of 1 L to an oyster meat of 1 kg, and at a standard pressure, heated the oyster meat for one hour at, for example, 90° C. or more. Then, the heating experiment heated an oyster essence (extract liquid) from which a solid content (boiled oyster) had been removed for a long time at, for example, 90° C. or more.

Then, in the heated state, the oyster essence was sampled every two hours (every one hour from 16 hours to 19 hours). To the sampled extract liquid, 100% ethanol was added such that the ethanol concentration of this extract liquid became, for example, 70%. Centrifugal ion (at 8100 G for 10 minutes) was performed on the extract liquid to obtain supernatant.

The supernatant was diluted by 100 times. The E6 concentration in the supernatant diluted by approximately 100 times was measured by the MRM (FIG. 11 and FIG. 12).

Figure 7:
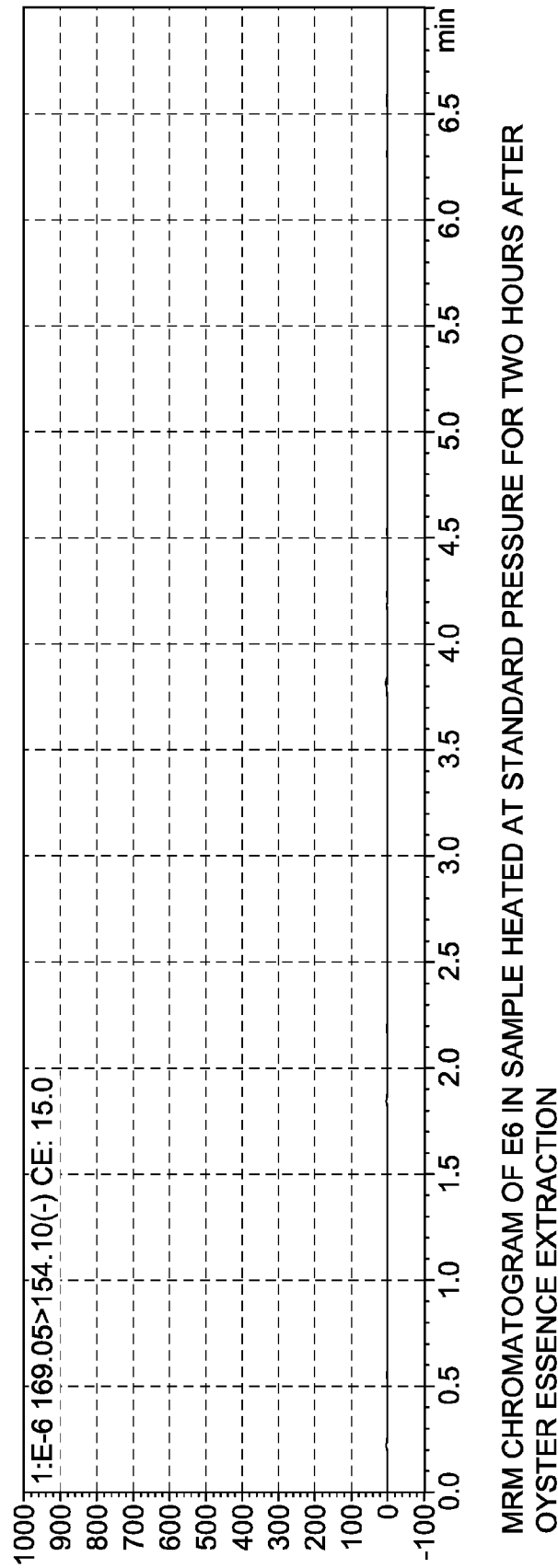
FIG. 7 is an explanatory view illustrating an MRM chromatogram of E6 in a sample heated at a standard pressure for two hours after an oyster essence extraction.

For example, FIG. 7 shows the MRM chromatogram of an E6 in a sample made by heating the extract liquid after the extraction of the oyster essence at a standard pressure for two hours.

As understood from FIG. 7, the peak was not observed at all at the holding time from 5.2 to 5.5 minutes. Accordingly, it can be understood that in the case where the extract liquid after the extraction of the oyster essence was heated at the standard pressure for two hours, the E6 was not detected.

Figure 8:
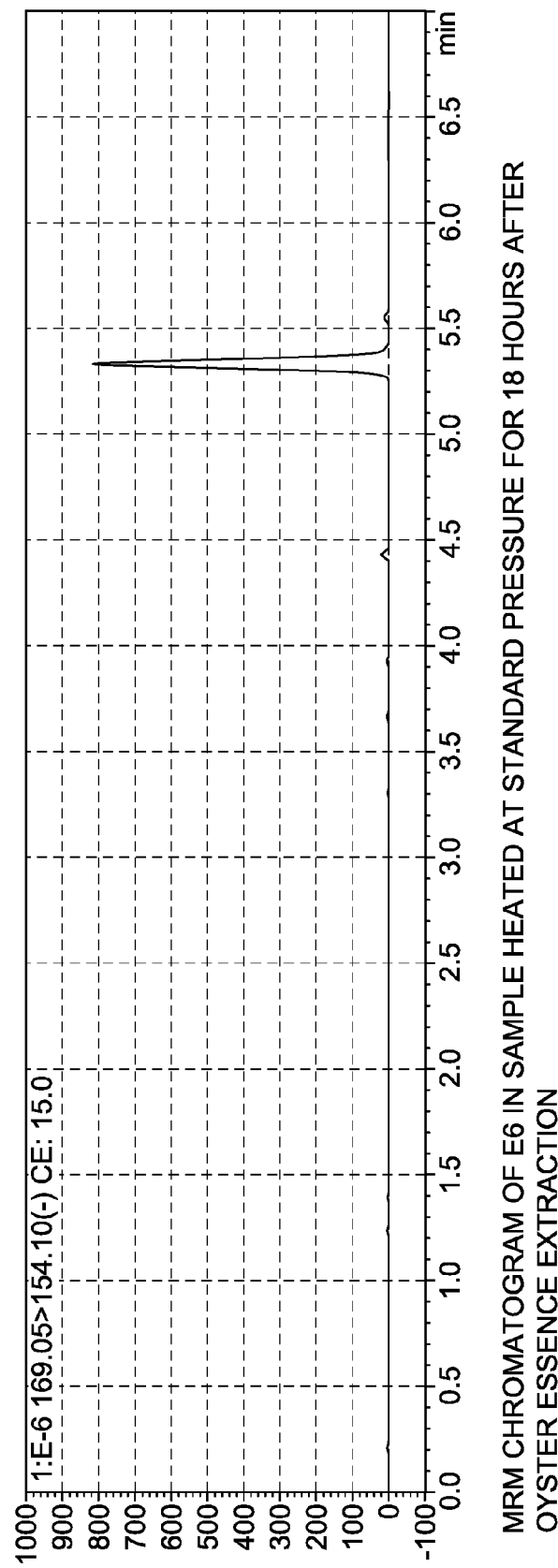
FIG. 8 is an explanatory view illustrating an MRM chromatogram of E6 in a sample heated at a standard pressure for 18 hours after an oyster essence extraction.

Next, FIG. 8 shows the MRM chromatogram of the E6 in the sample made by heating the extract liquid after the extraction of the oyster essence at a standard pressure for 18 hours. A single peak was confirmed at the holding time from 5.2 to 5.5 minutes. Accordingly, it can be understood that the E6 was detected (FIG. 8).

Figure 6:
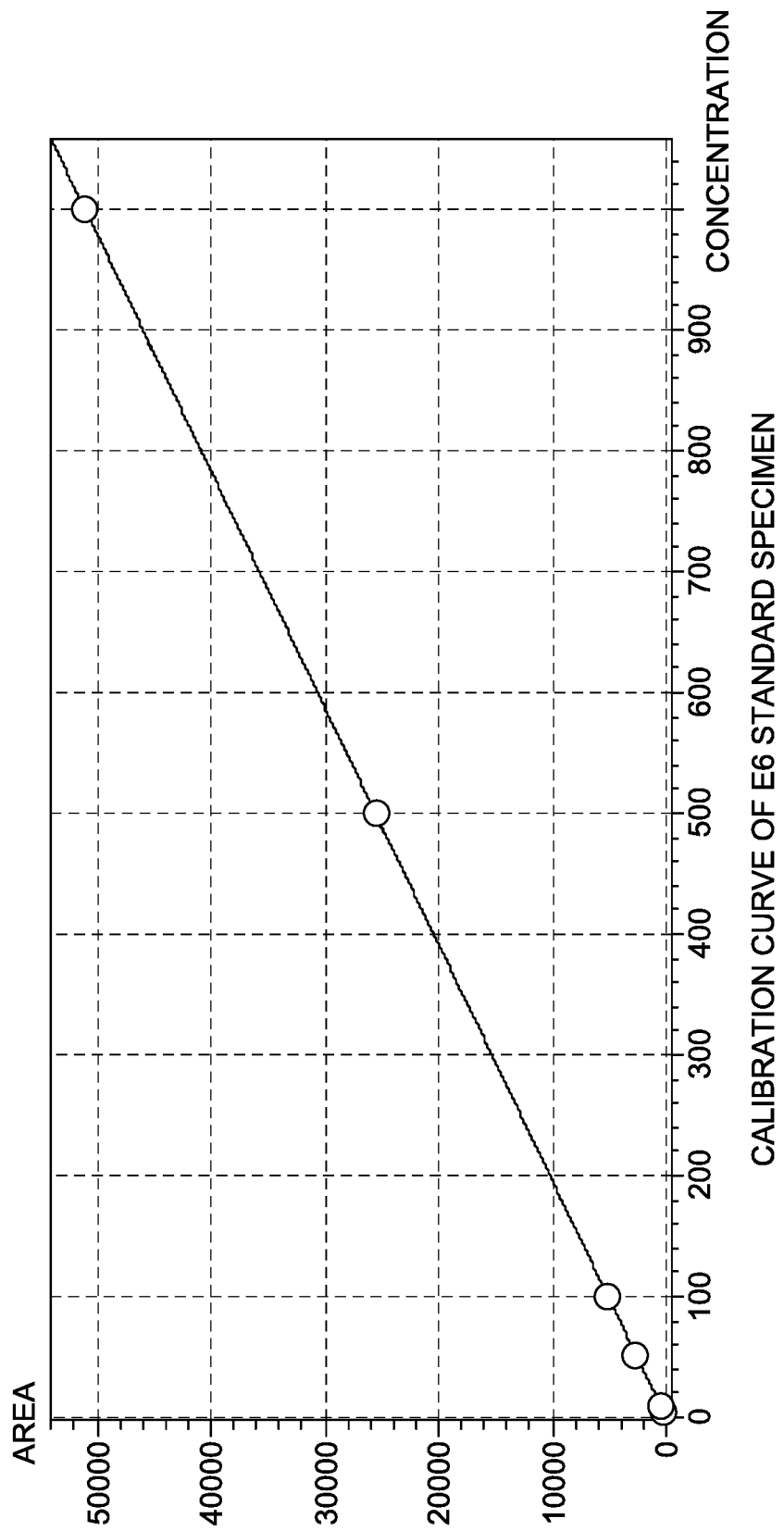
FIG. 6 is an explanatory view illustrating a calibration curve of an E6 standard specimen.

By the analyses of the calibration curve of the E6 standard specimen shown in FIG. 6 and the MRM chromatogram, it can be understood that the E6 concentration was 4.86±0.10 µg/mL (FIG. 11 and FIG. 12).

Furthermore, since the liquid measure when the extract liquid was heated for 18 hours was 125.38 g, the total amount of the E6 generated from the raw oyster of 1 kg was 609±13 µg.

The heating experiment with pressure added pure water of 20 L to the oyster of 20 kg and heated the oyster at the standard pressure for two hours. Then, the solid content (boiled oyster) was removed, and the liquid was heated at three atmospheric pressures for two hours using a pressure cooker (KAJIWARA, OAMVPα-C-08EL).

The liquid was sampled every one hour. To the sampled liquid, 100% ethanol was added such that the ethanol concentration became 70%. The centrifugation (at 8100 G for 10 minutes) was performed on the liquid to obtain supernatant. Furthermore, this supernatant was diluted by approximately 100 times. The E6 concentration in the sample was measured by the MRM, thus obtaining the results in FIG. 13.

Figure 9:
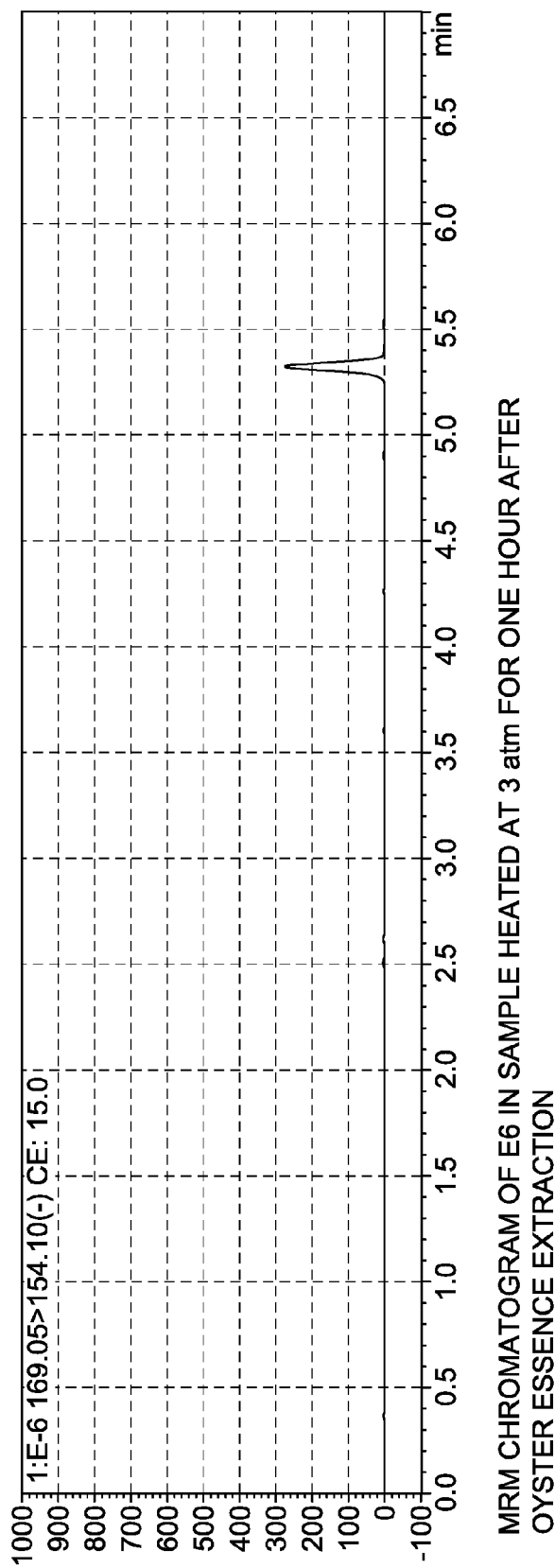
FIG. 9 is an explanatory view illustrating an MRM chromatogram of E6 in a sample heated at 3 atm for one hour after an oyster essence extraction.

FIG. 9 illustrates an MRM chromatogram of the E6 in the sample made by heating the extract liquid after the extraction of the oyster essence at 3 atm for one hour. A single peak was confirmed at the holding time from 5.2 to 5.5 minutes. Accordingly, the E6 was detected.

By the analyses of the calibration curve of the E6 standard specimen shown in FIG. 6 and the MRM chromatogram, it was found that the E6 concentration was 1.7±0.10 µg/mL (FIG. 13).

Since the liquid measure when the extract liquid was heated at three atmospheric pressures for one hour was 21.2 kg, the total amount of the E6 generated from the raw oyster of 20 kg was 36040±2120 µg. Converting the value in units of the raw oyster of 1 kg, the generated E6 was 1802±106 µg (FIG. 13).

Compared with the heating experiment with no pressure (the oyster extraction essence heated at the standard pressure for 18 hours), the heating experiment with pressure (the oyster extraction essence heated at three atmospheric pressures for one hour) was apparently exhibited low E6 concentration.

However, in the case of with pressure, since the amount of evaporation of water vapor in the sample is small and therefore the obtained liquid measure is large, the comparison in units of oyster of 1 kg, it can be understood that the case of with pressure exhibited an yield of the E6 of approximately three times as much as the case of with no pressure.

Figure 10:
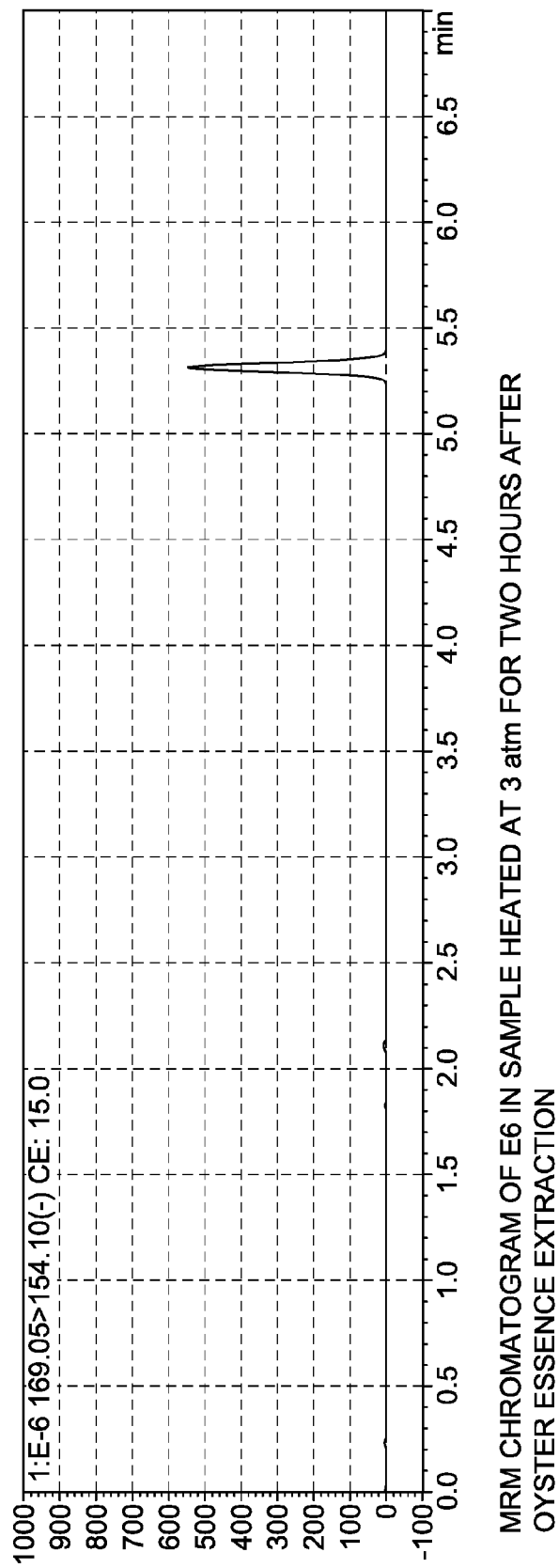
FIG. 10 is an explanatory view illustrating an MRM chromatogram of E6 in a sample heated at 3 atm for two hours after an oyster essence extraction.
Figure 16:
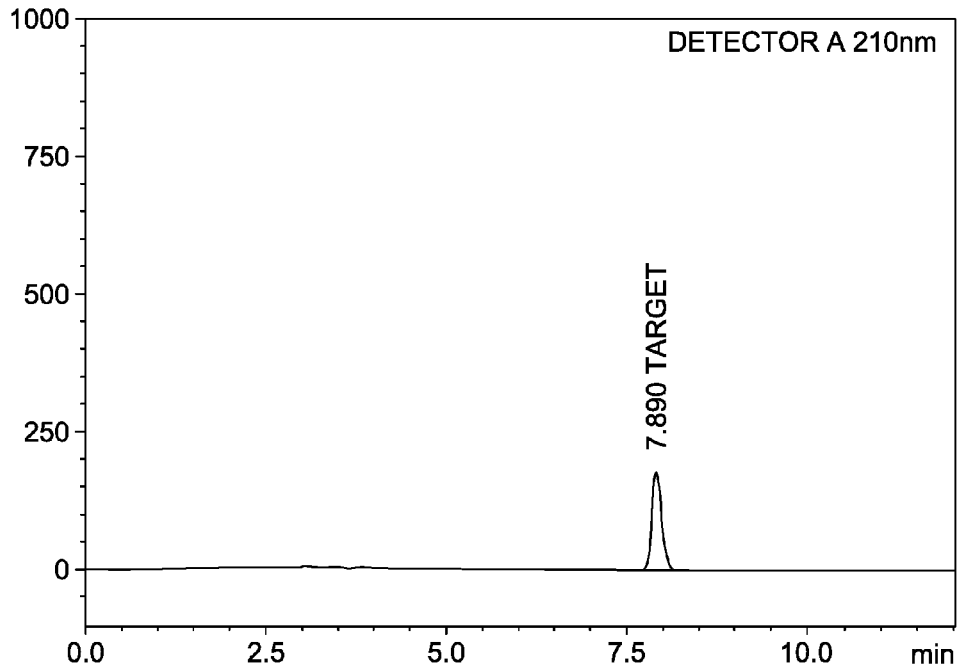
FIG. 16 is an explanatory view of an analysis report (1)
Figure 17:
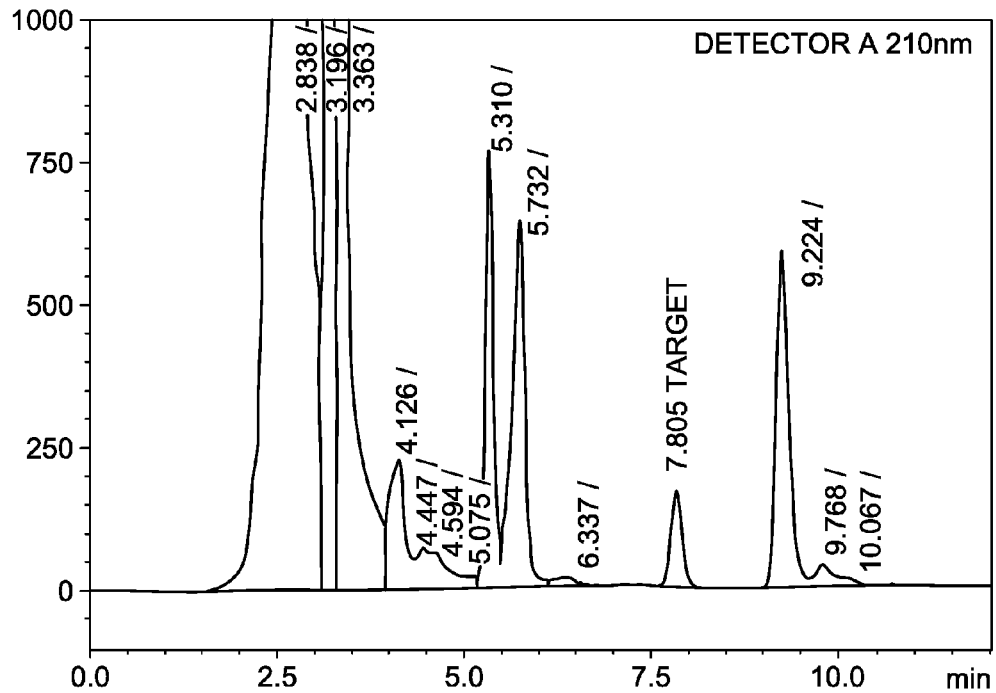
FIG. 17 is an explanatory view of an analysis report (2).

FIG. 10 shows the MRM chromatogram of the E6 in the sample made by heating the extract liquid after the extraction of the oyster essence at 3 atm for two hours.

A single peak was confirmed at the holding time from 5.2 to 5.5 minutes. Accordingly, the E6 was detected (FIG. 10).

By the analyses of the calibration curve of the E6 standard specimen shown in FIG. 6 and the MRM chromatogram, it was found that the E6 concentration was 3.5±0.39 µg/mL (FIG. 13).

Thus, since the liquid measure when the extract liquid was heated at three atmospheric pressures for one hour was 19.1 kg, the total amount of the E6 generated from the raw oyster of 20 kg was 66850±7449 µg. Converting the value in units of raw oyster of 1 kg, the generated E6 was 3343±373 µg (FIG. 13).

Compared with the heating experiment with no pressure (the oyster extraction essence heated at the standard pressure for 18 hours), the heating experiment with pressure (the oyster extraction essence heated at three atmospheric pressures for two hours) was apparently exhibited low E6 concentration.

However, in the case of with pressure, since the amount of evaporation of water vapor in the sample is small and therefore the obtained liquid measure is large, the comparison in units of oyster of 1 kg, the case of with pressure exhibited an yield of the E6 of approximately 5.5 times as much as the case of with no pressure.

From these results, it can be confirmed that the long time heating generates the E6 and further pressurizing the E6 results in much amount of collection.

Here, based on the above-described analysis results, this working example will be described in sum.

First, the raw oyster meat was pressurized, squashed, and liquefied. Then, in the liquefied raw oyster, at which concentration of 3,5-dihydroxy-4-methoxybenzyl alcohol was present or not was measured.

From the liquid made by pressurizing, squashing, and liquefying the raw oyster, 3,5-dihydroxy-4-methoxybenzyl alcohol was not detected at all. That is, in the cell of the raw oyster meat, 3,5-dihydroxy-4-methoxybenzyl alcohol was not found originally.

Next, as described above, the raw oyster meat and a liquid for extraction, for example, distilled water were put in an extraction container at the ratio of 1:1. The liquid for extraction containing the raw oyster meat was heated at one atmospheric pressure, for one hour, and at a high temperature of, for example, 92° C. to 94° C. and then extracted.

This is the extraction method for oyster meat essence what is called a heating extraction. This method was able to extract many active ingredients conventionally present in the raw oyster meat in the liquid for extraction. Here, the liquid for extraction from which many active ingredients present in the raw oyster meat are extracted and the raw oyster meat is removed is referred to as an extract liquid.

However, 3,5-dihydroxy-4-methoxybenzyl alcohol was not detected from the extract liquid as well. The other active ingredients were extracted.

Subsequently, a heating process was performed (at 92° C. to 94° C. similar to the above-described working example) on the extract liquid at one atmospheric pressure for two hours afterwards. Adding in the original extraction period, the heating process is three hours in total.

However, in the extract liquid on which the heating process was performed for three hours, the presence of 3,5-dihydroxy-4-methoxybenzyl alcohol was also not recognized as shown in FIG. 7.

Furthermore, the heating process was performed (at 92° C. to 94° C.) on the extract liquid at one atmospheric pressure for four hours (including the extraction period, five hours in total) to measure whether the extract liquid contained 3,5-dihydroxy-4-methoxybenzyl alcohol or not.

In this heating process (at 92° C. to 94° C.) for five hours, the presence of 3,5-dihydroxy-4-methoxybenzyl alcohol in the extract liquid was 0.09 (μg/ml), which is a value equal to or less than a quantitative limit as a value in concentration measurement. Accordingly, reliability that 3,5-dihydroxy-4-methoxybenzyl alcohol was surely present was not able to be obtained.

Subsequently, the heating process was performed (at 92° C. to 94° C.) on the extract liquid at one atmospheric pressure for six or five hours (including the extraction period, seven hours in total) to measure whether the extract liquid contained 3,5-dihydroxy-4-methoxybenzyl alcohol or not. However, the presence of 3,5-dihydroxy-4-methoxybenzyl alcohol in the extract liquid was 0.12 (μg/ml), which is also the value equal to or less than the quantitative limit as the concentration value. Accordingly, in this case as well, reliability that 3,5-dihydroxy-4-methoxybenzyl alcohol was surely present was not able to be obtained.

However, the healing process was performed on the extract liquid at one atmospheric pressure for six hours (including the extraction period, seven hours in total) at the high temperature of 98° C. to 100° C. To evaluate whether 3,5-dihydroxy-4-methoxybenzyl alcohol was present in the extract liquid or not, using an HPLC (Prominence LC-20A. Shimadzu), the presence of the E6 was measured (FIG. 14, FIG. 15, FIG. 16, and FIG. 17).

In the extract liquid, the value equal to or more than the quantitative limit as the concentration value, the presence of 3,5-dihydroxy-4-methoxybenzyl alcohol, was able to be found.

That is, in this case, the reliability in the presence of 3,5-dihydroxy-4-methoxybenzyl alcohol was able to be obtained.

Thus, in the case where the heating process was performed at the high temperature near 100° C., the heating process for six hours or more also was able to find 3,5-dihydroxy-4-methoxybenzyl alcohol, that is, the value equal to or more than the quantitative limit as the concentration value in the E6.

Furthermore, the heating process was performed (at 92° C. to 94° C.) on the extract liquid at one atmospheric pressure for eight hours (including the extraction period, nine hours) to measure whether the extract liquid contained 3,5-dihydroxy-4-methoxybenzyl alcohol or not.

However, the presence of 3,5-dihydroxy-4-methoxybenzyl alcohol was not able to be surely confirmed in this extract liquid as well. That is, the value of 0.29 (μg/ml) was obtained but after all the value was equal to or less than the quantitative limit for concentration measurement.

Next, the heating process was performed (at 92° C. to 94° C.) on the extract liquid at one atmospheric pressure for ten hours (including the extraction period, 11 hours) to measure whether the extract liquid contained 3,5-dihydroxy-4-methoxybenzyl alcohol or not.

Then, whether the presence of 3,5-dihydroxy-4-methoxybenzyl alcohol at the predetermined concentration was recognized in the extract liquid on which this long-time heating process (at 92° C. to 94° C.) was performed or not was confirmed.

Then, 0.54 (μg/ml), the value exceeding the quantitative limit for concentration measurement was able to be measured for the first time. It was confirmed that the extract liquid on which the heating process was performed for 11 hours in total apparently contained 3,5-dihydroxy-4-methoxybenzyl alcohol. This means that 3,5-dihydroxy-4-methoxybenzyl alcohol of 215.8 μg was generated from the oyster in units of 1 kg.

Furthermore, the heating process was performed on the extract liquid at one atmospheric pressure for 12 hours (adding in the original extraction period, 13 hours in total) to measure whether the extract liquid contained 3,5-dihydroxy-4-methoxybenzyl alcohol at the predetermined concentration or not.

Whether the presence of 3,5-dihydroxy-4-methoxybenzyl alcohol was recognized in the extract liquid or not was confirmed. Then, 0.86 (μg/ml), the increased value further exceeding the quantitative limit was able to be measured.

This means that 3,5-dihydroxy-4-methoxybenzyl alcohol of 288.4 μg was generated from the oyster in units of 1 kg.

Furthermore, the heating process was performed on the extract liquid at one atmospheric pressure for 14 hours (adding in the extraction period of one hour, 15 hours in total) to measure whether the extract liquid contained 3,5-dihydroxy-4-methoxybenzyl alcohol at the predetermined concentration or not.

Whether the presence of 3,5-dihydroxy-4-methoxybenzyl alcohol was recognized in the extract liquid or not was confirmed. Then, 1.42 (μg/ml), the value further exceeding the quantitative limit was able to be measured. Accordingly, it was confirmed that the long-time heating process caused further increased 3,5-dihydroxy-4-methoxybenzyl alcohol to be present in the extract liquid.

In this case, it means that 3,5-dihydroxy-4-methoxybenzyl alcohol of 373.9 µg was generated from the oyster in units of 1 kg.

Next, the heating process was performed on the extract liquid at one atmospheric pressure for 16 hours (adding in the extraction period, 17 hours) to measure whether the extract liquid contained 3,5-dihydroxy-4-methoxybenzyl alcohol at the predetermined concentration or not.

Whether the presence of 3,5-dihydroxy-4-methoxybenzyl alcohol was recognized in the extract liquid or not was confirmed. Then, 2.63 (µg/ml), the value increased again was able to be measured. Accordingly, it was confirmed that the long-time heating process caused 3,5-dihydroxy-4-methoxybenzyl alcohol to be present and increase.

In this case, it means that 3,5-dihydroxy-4-methoxybenzyl alcohol of 478.6 µg was generated from the oyster in units of 1 kg.

Furthermore, the heating process was performed on the extract liquid at one atmospheric pressure for 17 hours (adding in the extraction period, 18 hours) to measure whether the extract liquid contained 3,5-dihydroxy-4-methoxybenzyl alcohol at the predetermined concentration or not.

Whether the presence of 3,5-dihydroxy-4-methoxybenzyl alcohol was recognized in the extract liquid or not was confirmed. Then, 3.42 (µg/ml), the value increased again was able to be measured. Accordingly, the presence of 3,5-dihydroxy-4-methoxybenzyl alcohol was confirmed.

In this case, it means that 3,5-dihydroxy-4-methoxybenzyl alcohol of 519.5 µg was generated from the oyster in units of 1 kg.

Next, the heating process was performed on the extract liquid at one atmospheric pressure for 18 hours (including the extraction period, 19 hours) to measure whether the extract liquid contained 3,5-dihydroxy-4-methoxybenzyl alcohol at the predetermined concentration or not.

Then, the value of 4.86 (µg/ml), the further increased concentration value, was able to be measured as shown in FIG. 8.

This means that 3,5-dihydroxy-4-methoxybenzyl alcohol of 609.3 µg was generated from the oyster in units of 1 kg.

Furthermore, the long-time heating process was performed on the extract liquid at one atmospheric pressure for 19 hours (adding in the extraction period of one hour, 20 hours) to measure whether the extract liquid contained 3,5-dihydroxy-4-methoxybenzyl alcohol or not. Whether the presence of 3,5-dihydroxy-4-methoxybenzyl alcohol at the predetermined concentration was recognized in the extract liquid or not was confirmed. Then, the value, 6.49 (µg/ml), was able to be measured. Accordingly, it was confirmed that further increased 3,5-dihydroxy-4-methoxybenzyl alcohol was present.

In this case, it means that 3,5-dihydroxy-4-methoxybenzyl alcohol of 581.3 µg was generated from the oyster in units of 1 kg.

Thus, the following is confirmed. Originally, the raw oyster did not contain 3,5-dihydroxy-4-methoxybenzyl alcohol at all. 3,5-dihydroxy-4-methoxybenzyl alcohol was also not present in and detected from the extract liquid on which the heating extraction of the oyster meat essence was performed at one atmospheric pressure for one hour at all. The longer the heating time of this extract liquid extremely or the closer the heating temperature to 100° C., 3,5-dihydroxy-4-methoxybenzyl alcohol is generated and increased.

Consequently, when performing the heating process on the extract liquid of the oyster meat essence at one atmospheric pressure for 19 hours (including the extraction period of one hour, 20 hours), assuming that the specific gravity of the extract liquid as 1,3,5-dihydroxy-4-methoxybenzyl alcohol of 581 µg (6.49 µg×89.57 g) was generated from the oyster in units of 1 kg.

Furthermore, as described above, when performing the heating process on the extract liquid at one atmospheric pressure for two hours to eight hours, 3,5-dihydroxy-4-methoxybenzyl alcohol at the predetermined concentration was not detected at all. However, as understood from FIG. 13, when performing the heating process on the extract liquid (extracted liquid from which the raw oyster had been removed) at three atmospheric pressures for one hour, the value of 1.7 (µg/ml) was obtained as the concentration of 3,5-dihydroxy-4-methoxybenzyl alcohol. From this value, assuming that the liquid measure of 21.2 kg was obtained from the raw oyster of 20 kg and the specific gravity of the extract liquid as 1, the heating process at three atmospheric pressures for one hour generated 3,5-dihydroxy-4-methoxybenzyl alcohol of 1820 µg from the oyster in units of 1 kg.

Furthermore, when performing the heating process on the extract liquid at three atmospheric pressures for two hours, the value of 3.5 (µg/ml) was obtained as the concentration of 3,5-dihydroxy-4-methoxybenzyl alcohol. From this value, assuming that the liquid measure of 19.1 kg was obtained from the oyster meat of 20 kg and the specific gravity of the extract liquid as 1, the heating process at three atmospheric pressures for two hours generated 3,5-dihydroxy-4-methoxybenzyl alcohol of 3342.5 µg from the oyster in units of 1 kg.

When performing the heating process at a pressurized state equal to or more than one atmospheric pressure for a predetermined time, for example, 50 minutes or more, combined with an increase in the heating temperature by the pressurization, the value equal to or more than the quantitative limit as the concentration value of 3,5-dihydroxy-4-methoxybenzyl alcohol can be found.

Thus, the following has been proved. 3,5-dihydroxy-4-methoxybenzyl alcohol, which originally cannot be found in the raw oyster meat, is clearly generated by heating and/or pressurization process(es) on the extract liquid of the oyster meat essence on which the heating extraction has been performed. Moreover, it has been proved that the longer heating period increases the generated 3,5-dihydroxy-4-methoxybenzyl alcohol.

Furthermore, the following can be confirmed. When performing the pressurization process at three atmospheric pressures, even if the process time is short time, 3,5-dihydroxy-4-methoxybenzyl alcohol is generated.

The invention claimed is:

1. A generation method for generating 3,5-dihydroxy-4-methoxybenzyl alcohol from an oyster meat, the generation method consisting essentially of:
    putting raw oyster meat from which 3,5-dihydroxy-4-methoxybenzyl alcohol is not detected in a raw state in an extraction container with water as the sole solvent and heating at 90° C. or more for one hour or more to extract oyster meat essence liquid;
    heating the oyster meat essence extract liquid at 98° C. to 100° C. for six hours or more,
    to generate 3,5-dihydroxy-4-methoxybenzyl alcohol from the oyster meat essence extract liquid on which the heating process has been performed.

2. A generation method for generating 3,5-dihydroxy-4-methoxybenzyl alcohol from an oyster extract, the generation method consisting essentially of:
    providing an oyster meat essence extract liquid prepared by putting raw oyster meat from which 3,5-dihydroxy-4-methoxybenzyl alcohol is not detected in a raw state in an extraction container with water as the sole solvent and heating at 90° C. or more for one hour or more to obtain the oyster meat essence extract liquid;
    heating the oyster meat essence extract liquid at 92° C. or more for at least ten hours or more,
    to generate 3,5-dihydroxy-4-methoxybenzyl alcohol from the oyster meat essence extract liquid on which the heating process has been performed.

3. A generation method for generating 3,5-dihydroxy-4-methoxybenzyl alcohol from an oyster meat, the generation method consisting essentially of:
    putting raw oyster meat from which 3,5-dihydroxy-4-methoxybenzyl alcohol is not detected in a raw state in an extraction container with water as the sole solvent and heating at 90° C. or more for one hour or more to extract oyster meat essence liquid;
    heating the oyster meat essence extract liquid in a pressurized state of three atmospheric pressures or more at 135° C. or more for at least one hour or more,
    to generate 3,5-dihydroxy-4-methoxybenzyl alcohol from the oyster meat essence extract liquid heated in the pressurized state.

4. A generation method for generating 3,5-dihydroxy-4-methoxybenzyl alcohol from an oyster extract, the generation method consisting essentially of:
    providing an oyster meat essence extract liquid prepared by putting raw oyster meat from which 3,5-dihydroxy-4-methoxybenzyl alcohol is not detected in a raw state in an extraction container with water as the sole solvent and heating at 90° C. or more for one hour or more to obtain the oyster meat essence extract liquid;
    heating the oyster meat essence extract liquid in a pressurized state of three atmospheric pressures or more at 135° C. or more for at least one hour or more,
    to generate 3,5-dihydroxy-4-methoxybenzyl alcohol from the oyster meat essence extract liquid heated in the pressurized state.

\* \* \* \* \*